US00PP19381P2

(12) United States Plant Patent
Lyrene

(10) Patent No.: US PP19,381 P2
(45) Date of Patent: Oct. 28, 2008

(54) SOUTHERN HIGHBRUSH BLUEBERRY PLANT NAMED 'FLX-2'

(50) Latin Name: *Vaccinium corymbosum*
Varietal Denomination: FLX-2

(75) Inventor: Paul M. Lyrene, Micanopy, FL (US)

(73) Assignee: The University of Florida Board of Trustees, Gainesville, FL (US)

( * ) Notice: Subject to any disclaimer, the term of this patent is extended or adjusted under 35 U.S.C. 154(b) by 0 days.

(21) Appl. No.: 11/977,635

(22) Filed: Oct. 25, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Jondle & Associates, P.C.

(57) ABSTRACT

A southern highbush blueberry (*Vaccinium corymbosum*) cultivar particularly distinguished by having a very low chilling requirement (300 hours below 7° C.) with leaves that are evergreen to semi-evergreen and smaller than typical southern highbush leaves with a striking blue-green color, plants flowers early in the spring and produces medium sized, light-blue colored berries that have excellent flavor and texture is disclosed.

4 Drawing Sheets

Genus and species: *Vaccinium corymbosum* L.
Variety denomination: 'FLX-2'.

BACKGROUND OF THE NEW PLANT

The invention relates to a new and distinct variety of southern highbush blueberry (*Vaccinium corymbosum* L.) hybrid plant named 'FLX-2.' 'FLX-2' is expected to be used as a patio plant grown either in pots or in the ground for its attractive form and foliage and for its edible berries. 'FLX-2' is a southern highbush blueberry clone distinguished by its low chilling requirement, its blue-gray leaves, and by its medium-size, blue berries that ripen from mid-April through mid-May when grown in central and north Florida. Several dozen plants of 'FLX-2' have been propagated by softwood cuttings at Gainesville, Fla., and the resulting plants have all been phenotypically indistinguishable from the original plant.

'FLX-2' originated as a seedling from the cross of the proprietary female parent, 'FL 92-9' (unpatented) with the male parent, 'Sunshineblue' (unpatented) and was made as part of the University of Florida breeding program in a greenhouse at Gainesville, Fla. in March, 1992. The seedling was first fruited in a high-density field nursery in the spring of 1994. In January, 1998, rooted cuttings from the original plant were used to establish a 15-plant clonal plot in a test planting at Windsor in north Florida. In January 2000, 12 rooted cuttings were sent to a nursery in Lowell, Oreg. where the plants were further propagated to produce 50 plants that were evaluated in 3-gallon pots, starting in January 2002.

SUMMARY OF THE INVENTION

The following are the most outstanding and distinguishing characteristics of this new cultivar when grown under normal horticultural practices in Florida.

1. A very low chilling requirement;
2. Leaves that are evergreen to semi-evergreen and are smaller than typical southern highbush with a striking blue-green color; and 3. Flowering early in the spring to produce medium sized, light-blue colored berries with excellent flavor and texture

DESCRIPTION OF THE PHOTOGRAPHS

The color chart used in this specification is "The Pantone Book of Color", by Leatrice Eiseman and Lawrence Herbert. (1990). Harry N. Abrams, Inc., Publishers, N.Y. Where colors in the drawings differ from the Pantone color designations in the descriptions, the Pantone color designations are accurate. The colors shown are as true as can be reasonably obtained by conventional photographic procedures.

Figure 1:
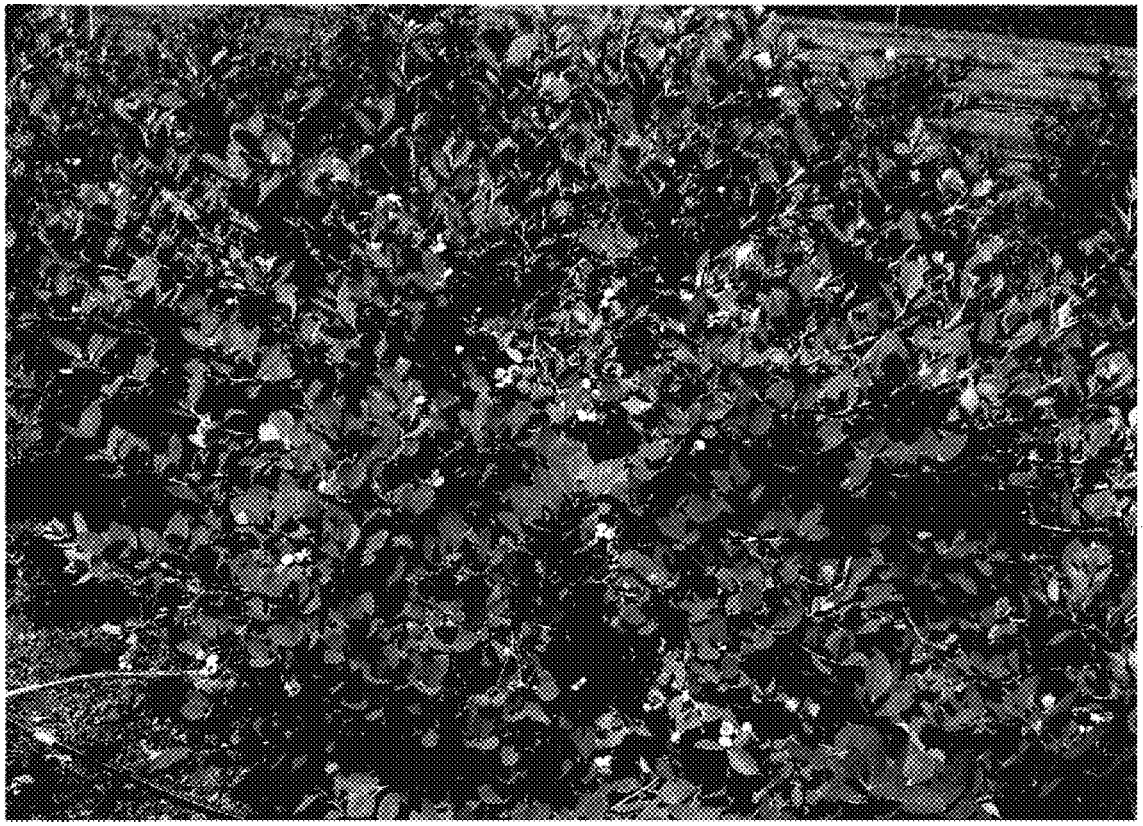
FIG. 1 shows a 4-year old plot of 'FLX-2' plants in a test block in western Oregon. The dense blue-green canopy and somewhat spreading growth habit are visible.
Figure 2:
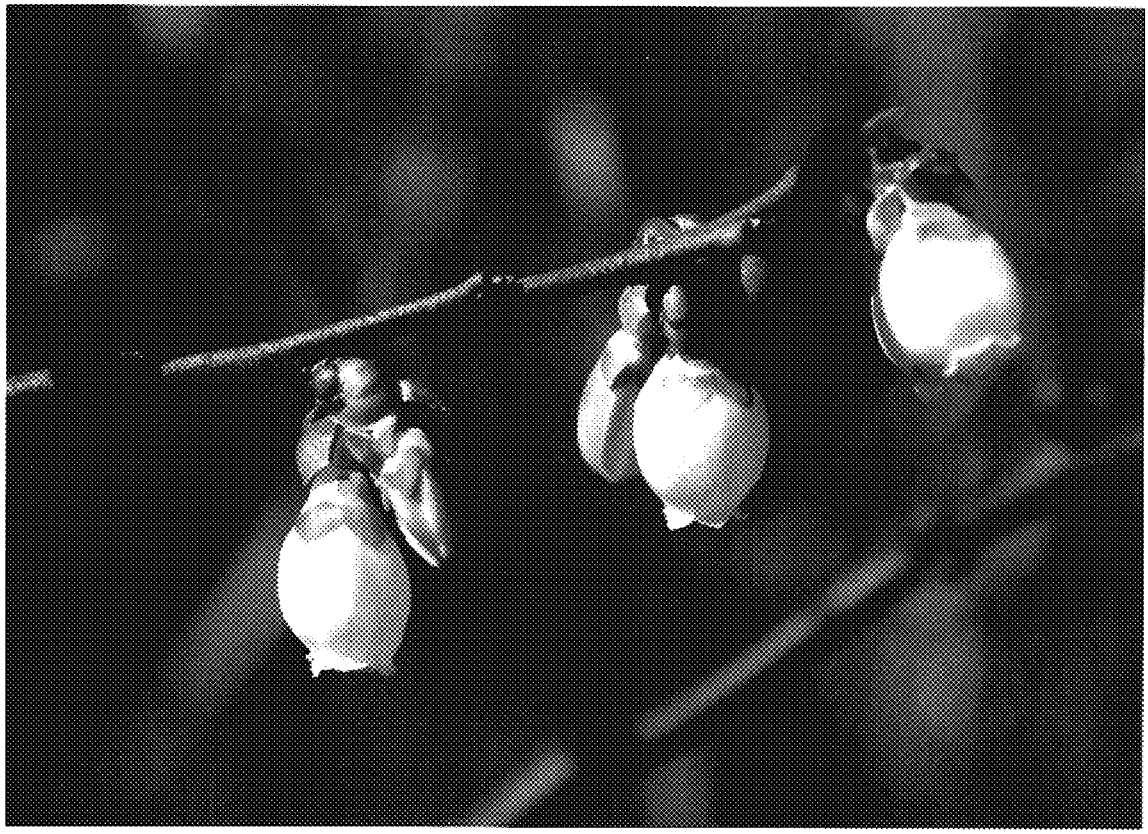
FIG. 2 shows several clusters of flowers on 'FLX-2' in early February in Florida. The berries are pink before opening, especially in cold weather, but become white as they mature.
Figure 3:
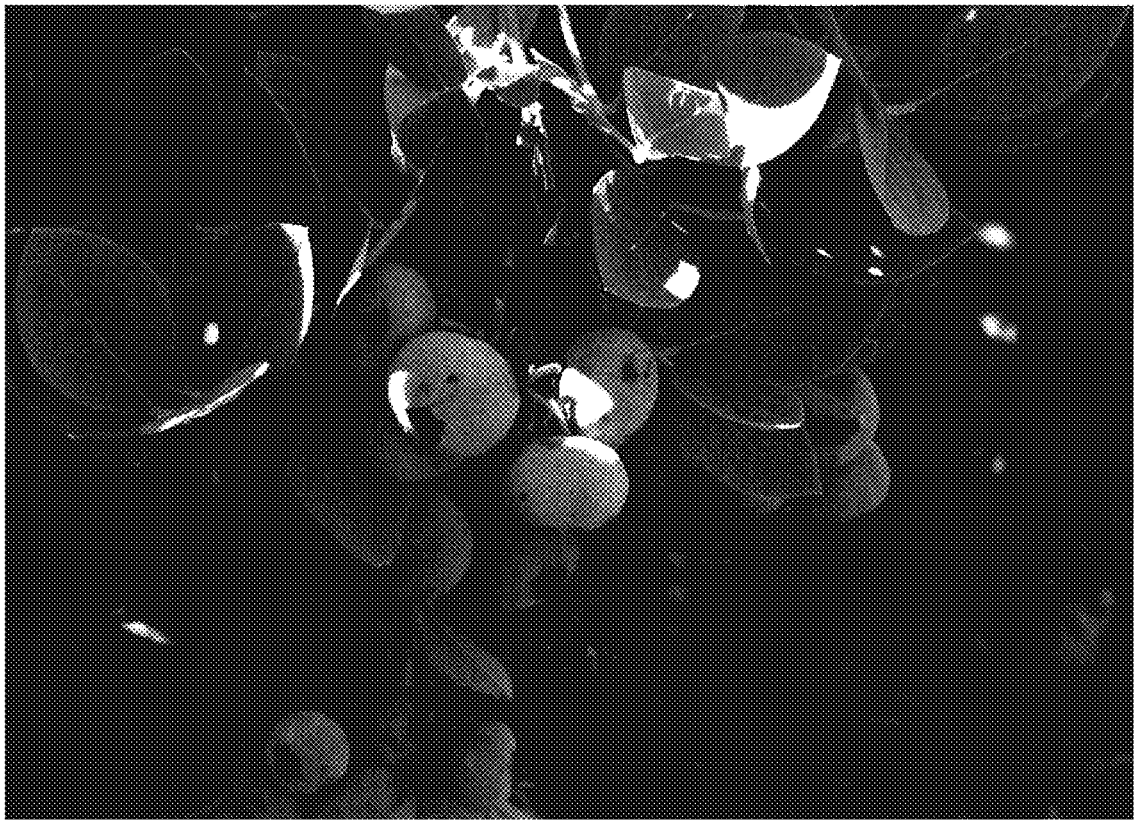

FIG. 3 shows clusters of ripe berries on a field-grown plant. The berries have a light-blue color and are somewhat flattened. The bluish color of the leaves is also shown.

Figure 4:
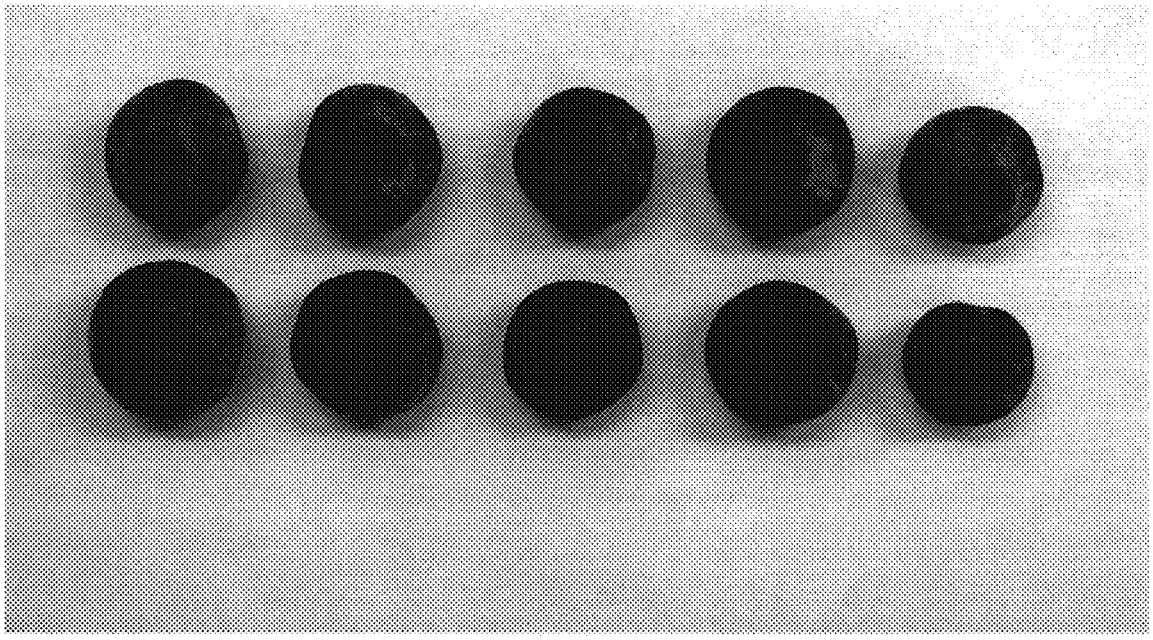

FIG. 4 shows berries at close range. The berries are darker than in FIG. 3 due to handling.

DESCRIPTION OF THE NEW CULTIVAR

The following detailed description sets forth the distinctive characteristics of 'FLX-2'. The data which defines these characteristics were collected from asexual reproductions carried out in Florida. The plant history was taken on 9.5 year-old plants. The following descriptions relate to plants grown in the field in north Florida (Windsor, Fla.). Color designations are from "The Pantone Book of Color" (by Leatrice Eiseman and Lawrence Herbert; Harry N. Abrams, Inc. Publishers, New York, 1990). Where the Pantone color designations differ from the colors in the Drawings, the Pantone colors are accurate.

DETAILED BOTANICAL DESCRIPTION

Classification:

*Family.*—Ericaceae.

*Botanical.*—*Vaccinium corymbosum* L.

*Common name.*—Southern Highbush Blueberry.

Parentage:

*Female parent.*—'FL 92-9', a proprietary southern highbush blueberry plant (unpatented).

*Male parent.*—'Sunshineblue' a southern highbush blueberry plant (unpatented).

Market class: 'FLX-2' produces an attractive patio plant with a medium yield of high quality berries; it is not intended to be planted for commercial berry production Plant:

*General.*—Bush characteristics were taken from a plot of twenty 9.5 year-old-plants growing in a test plot in a commercial field near Windsor in northeast Florida.

*Plant height.*—1.6 cm.

*Canopy* (*diameter measured at widest part of the bush*).—1.7 m.

*Plant vigor.*—High; more vigorous and faster growing than 'Sunshineblue'.

*Growth habit.*—Between upright and spreading.

*Flower bud density* (*number*) *along flowering twigs in January.*—High.

*Twigginess.*—Medium to high.

*Tendency toward evergreenness.*—High.

*Chilling requirement.*—200 to 300 hours below 7°.

*Cold hardiness.*—Flowers and fruit are hardy to −3° C., the plant is hardy to −15° C. during winter dormancy.

*Productivity.*—In northeast Florida, 'FLX-2' produces 3 to 5 pounds of berries per bush on plants 3 years old or older.

*Ease of propagation.*—'FLX-2' is easy to propagate from softwood cuttings; the plant survive and grow well in nursery beds.

Trunk and branches:

*Suckering tendency.*—Medium to high; nine-year-old plants have an average of 15 majors canes rising from a crown 30 cm in diameter.

*Surface texture* (*or strong, 6-month-old shoots observed in August*).—Smooth.

*Surface texture* (*of strong, 1-year-old wood observed in August*).—Rough except smooth in areas where the bark has recently exfoliated.

*Surface texture* (*of 3-year-old and older wood*).—Smooth, but vertical cracks developing on older wood produce a rough surface.

*Color of new twigs observed in August in the field.*—"Pale Star", Pantone 12-0626.

*Color of 1-year-old, rough bark observed in August.*—"Smoke Gray", Pantone 14-1209.

*Color of 3-year-old rough-textured canes.*—"Moonlight", Pantone 15-1309.

*Internode length on medium, upright shoots measured in August.*—0.9 cm.

Leaves:

*Length, mean* (*including petiole, from tip of petiole to end of blade*).—4.7 cm.

*Width, means* (*at widest point*).—2.5 cm.

*Shape.*—Ovate, terminating in a very short dew tip, 0.03 cm long which is visible at 15X under a microscope.

*Margin.*—Minutely serrate along the petiolar half of the leaf blades; otherwise entire.

*Color.*—Upper surface: "Silver Green", Pantone 12-6204. Lower surface: "Fog Green", Pantone 13-0210.

*Pubescence on upper surface of leaves.*—Absent.

*Pubescence on the lower surface of leaves.*—Absent.

*Pubescence on margins.*—Absent.

*Relative time of leading versus flowering.*—In commercial fields in North Florida, where it is sprayed with hydrogen cyanomide in midwinter, 'FLX-2' normally produces new leaves at the time of flowering.

Flowers:

*Arrangement.*—Flowers are arranged alternately along a short, leafless, deciduous branch.

*Fragrance.*—Little or none.

*Shape.*—Urceolate.

*Flowering period.*—Mean date of 50% open flowers in Windsor, Fla. is February 17; averages 10 days before 'Star' (U.S. Plant Pat. No. 10,675).

*Cluster* (*tight, medium, loose*).—Loose.

*Average number of flowers per cluster.*—5.

*Pedicel.*—Length at time of anthesis: 0.4 cm. Color: "Periodot", Pantone 17-0336.

*Peduncle.*—Length at time of anthesis: Highly variable; median is 0.6 cm. Color: "Periodot", Pantone 17-0336.

*Calyx.*—Cup diameter at anthesis (tip of lobe to tip of opposite lobe): 0.5 cm; calyx lobes are unusually short for a southern highbush blueberry cultivar. Surface texture: Smooth. Color of anthesis: "Peridot", Pantone 17-0336.

*Corolla.*—Length of tube: 0.9 cm. Diameter of tube (at widest point): 0.6 cm to 0.7 cm. Aperture diameter: 0.3 cm. Surface texture: Smooth. Color at anthesis: "Parchment"; Pantone 13-0908. Length (from pedicel attachment point to corolla tip excluding the pedicel): 1.1 cm to 1.2 cm.

Reproductive organs:

*Style length* (*top of ovary to stigma tip*).—0.8 cm.

*Location of tip of stigma relative to lip of the corolla.*—Stigma tip is about 0.1 cm inside of the end of the corolla tube; if the style where 0.1 cm longer, the stigma tip would extend just to the outer edge of the corolla tube.

*Pistil color at anthesis.*—"Herbal Green", Pantone 15-0336.

*Pollen.*—General: The pollen includes some tetrads in which one or two spores have aborted; although pollen staining appears to be slightly below normal, pollen fertility is not expected to be a problem in commercial fields. Abundance of shed: High. Staining with 2% acetocarmine (a measure of potential pollen fertility): 95%. Color of dried pollen: "Yolk Yellow", Pantone 14-0846.

Self fruitfulness: low; berry size and fruit set are both increased substantially by cross-pollination.

Fruit:

*Mean date of first commercial harvest* (*25% of berries ripe*).—April 26.

*Mean date of mid-harvest.*—May 2.

*Mean date of last harvest.*—May 20.

*Diameter of calyx aperture on mature berry.*—0.7 cm.

*Size and shape of calyx lobes on mature berry.*—Very small; calyx dish very shallow and wide.

*Pedicel length on ripe berry.*—0.5 cm.

*Peduncle length on ripe berry.*—Highly variable; 1.0 cm.

*Detachment force for ripe berries.*—Medium to low.

*Number of berries per cluster.*—5.

Berry:

*Cluster* (*tight, medium, or loose*).—Loose.

*Weight* (*on well-pruned plants*).—2.3 g per berry compared to 1.8 g per berry for 'Star' (U.S. Plant Pat. No. 10,675).

*Height.*—1.4 cm to 1.5 cm.

*Width.*—1.5 cm.

*Shape.*—Spherical.

*Surface color of mature berries while on the plant.*—"Storm Gray", Pantone 15-4003.

*Surface color of the berries after harvesting and packing.*—"Frost Gray", Pantone 17-0000.

*Surface color of ripe berry after polishing.*—"Jet Black", Pantone 19-0303.

*Internal flesh color of ripe berry.*—"Frozen Dew", Pantone 13-0513.

*Surface wax.*—Medium in amount and in persistence during handling of the berry.

*Pedicel scar.*—Very small and dry.

*Firmness.*—Very high.

*Flavor.*—Very sweet and low in acid.

*Texture.*—Good; small seeds, very juicy and thin skinned.

Seeds:

*Color of dried seeds.*—"Hazel", Pantone 17-1143.

*Weight of well-developed dried seed.*—0.49 mg per seed.

*Length of well-developed dried seed.*—0.1 cm.

*Width of well-developed dried seed.*—0.1 cm.

Resistance to Diseases, Insects and Mites: 'FLX-2' has grown vigorously and shows excellent bush survival in the field; has above-average resistance to root rot (*Phytophthora cinnamomi*) and stem blight (*Botryosphaeria dothidia*); have shown no signs of cane canker (*Botryosphaeria corticis*) susceptibility in the field; and fungal leaf spots that are common on highbush blueberries grown in Florida are easily controlled by approved fungicides.

COMPARISON WITH PARENTAL AND KNOWN CULTIVARS

'FLX-2' differs from the proprietary female (seed) parent 'FL 92-9' (unpatented) in that 'FLX-2' has smaller leaves, a greater tendency to retain leaves through the winter than 'FL 92-9'. Additionally, 'FLX-2' has a more pronounced blue color of the leaves and fruit and a shorter, more spreading growth habit that 'FL92-9'.

'FLX-2' differs from the male (pollen) parent and commercial variety 'Sunshineblue' (unpatented) in that 'FLX-2' has larger berries, larger leaves and a more pronounced blue color to the leaves and fruit than 'Sunshineblue'.

I claim:

1. A new and distinct cultivar of southern highbush blueberry plant as shown and described herein.

* * * * *

UNITED STATES PATENT AND TRADEMARK OFFICE

CERTIFICATE OF CORRECTION

PATENT NO. : PP 19,381 P2
APPLICATION NO. : 11/977635
DATED : October 28, 2008
INVENTOR(S) : Paul M. Lyrene It is certified that error appears in the above-identified patent and that said Letters Patent is hereby corrected as shown below:

Title Page Item [54]
error in the Title of the Letters Patent, where "SOUTHERN HIGHBRUSH BLUEBERRY PLANT NAMED 'FLX-2'" should read, -- SOUTHERN HIGHBUSH BLUEBERRY PLANT NAMED 'FLX-2' --.

Signed and Sealed this

Thirteenth Day of January, 2009

JON W. DUDAS
*Director of the United States Patent and Trademark Office*